United States Patent
Togashi et al.

(10) Patent No.: US 6,459,918 B1
(45) Date of Patent: Oct. 1, 2002

(54) BRAIN ELECTRODE SECURING DEVICE

(75) Inventors: Akio Togashi, Moroyama-machi; Kenji Takano, Tokyo-to; Takaaki Musha, Kawagoe, all of (JP)

(73) Assignee: Tomy Kogyo Co., Ltd., Wako (JP)

( * ) Notice: Subject to any disclaimer, the term of this patent is extended or adjusted under 35 U.S.C. 154(b) by 15 days.

(21) Appl. No.: 09/653,546

(22) Filed: Aug. 31, 2000

(30) Foreign Application Priority Data

Feb. 24, 2000 (JP) ......................................... 2000-047371

(51) Int. Cl.[7] ............................................... A61B 5/042

(52) U.S. Cl. ...................... 600/378; 606/129; 606/130; 607/116

(58) Field of Search ............................ 600/378; 66/129, 66/130; 607/116, 139

(56) References Cited

U.S. PATENT DOCUMENTS 3,841,310 A * 10/1974 Goldstein .................... 600/378

* cited by examiner

*Primary Examiner*—Lee Cohen
(74) *Attorney, Agent, or Firm*—Varndell & Varndell, PLLC (57) ABSTRACT

The present invention relates to a device for inserting a brain electrode which makes it easy to install the device and to insert the brain electrode and yet allows the electrode to be inserted with sufficient precision. The present invention is a brain electrode securing device, in which an electrode-wire-type electrode held by an electrode holder is inserted into the brain through a hole formed in the skull for the purpose of measuring changes in electrical potential at an electrode at a measuring location inside the brain, and the device comprises a casing which is securely mounted on the skull so as to surround the aforementioned hole, an electrode holder which is arranged so as to slide freely in relation to the aforementioned casing, and a screw rod which is screwed approximately to the center of the electrode holder and is supported so as to rotate freely in relation to the aforementioned casing.

4 Claims, 8 Drawing Sheets

BRAIN ELECTRODE SECURING DEVICE

BACKGROUND OF THE INVENTION

1. Field of the Invention

The present invention is a brain electrode securing device, and particularly to a brain electrode securing device which holds an electrode inserted into the brain in order to measure changes in electrical potential in the nerve cells in the brains of small animals such as mice and rats and to stimulate the aforementioned brain nerve cells electrically.

2. Description of the Related Art

In order to measure changes in electrical potential in the nerve cells in the brains of small animals such as mice and rats and to stimulate the aforementioned brain nerve cells electrically, it is necessary to open a hole in the skull of the small animal and to insert an electrode through the aforementioned hole as far as a prescribed location inside the brain. This electrode is secured to the skull by means of a brain electrode securing device.

Figure 8:
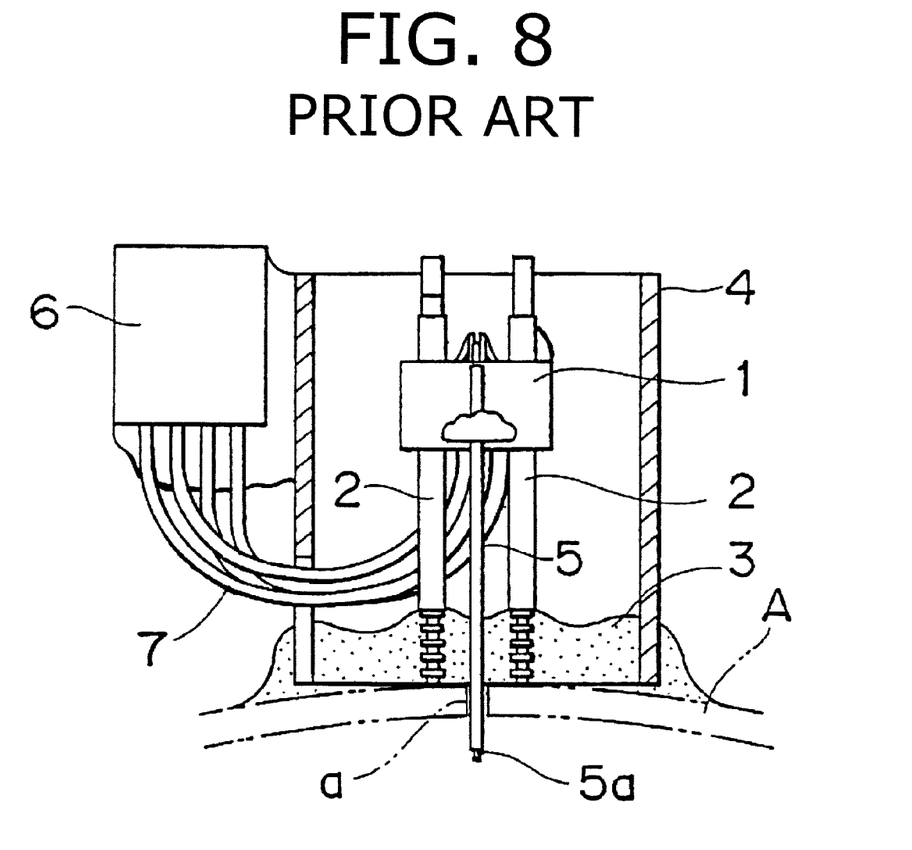
FIG. 8 is a general view showing the device for securing the brain electrode provided above.

A brain electrode securing device of this type as shown in FIG. 8 was provided. In this brain electrode securing device, two screw rods 2,2 were screwed into the electrode holder 1 and the lower ends of the screw rods 2,2 were arranged with the hole a opened in the skull interposed between them and the lower ends of the aforementioned screw rods 2,2 were rotatably secured, by means of dental cement 3 etc., to the hole a opened in the skull A. Furthermore, in this brain electrode securing device, the connector casing 4 is mounted on the skull A so as to surround the screw rods 2,2, this connector casing 4 is secured to the skull A by means of dental cement 3 or the like, and the connector 6 is installed in the aforementioned connector casing 4 and the upper end of the electrode wire 5 is connected to the connector 6 using the lead 7. In such a brain electrode securing device, the electrode holder 1 is lowered by rotating the screw rods 2,2, and the tip (the electrode) 5a of the electrode wire 5 is Inserted to the prescribed position inside the brain.

However, in the aforementioned brain electrode securing device, it is necessary to arrange the electrode wire 5 perpendicularly in relation to the skull A and, because of this, the operation to install the two screw rods 2,2, in which the 2 screw rods 2,2 have to be secured in relation to the surface of the skull while their position is adjusted individually in a perpendicular direction, is laborious.

Furthermore, with the brain electrode securing device, a laborious operation is required in which, after the screw rods 2,2 have been secured, the connector casing 4 has to be fixed on the skull A, the aforementioned connector casing has to be secured and then the electrode wire 5 has to be connected using the lead 7.

In addition, in the aforementioned brain electrode securing device, when the electrode 5a is being inserted into the brain, not only is it necessary to perform a laborious operation in which the electrode holder 1 is lowered by making each of the 2 screw rods rotate slightly in relation to one another, while this operation is being performed the electrode holder 1 shakes as it is lowered so that the electrode 5 which is held in the aforementioned electrode holder 1 sways from side to side and it is difficult to perform the insertion with adequate precision.

SUMMARY OF THE INVENTION

The object of the present invention is to provide a brain electrode securing device in which the operation to install the device for securing the brain electrode and the operation to insert the electrode are easy and yet the electrode can be inserted with sufficient precision.

The present invention aimed at achieving the aforementioned object is a brain electrode securing device, in which an electrode-wire-type electrode held by an electrode holder is inserted into the brain through a hole formed in the skull in order to measure changes in electrical potential at an electrode at a measuring location inside the brain, comprising:

- a casing which is fixedly mounted on the skull so as to surround the aforementioned hole;
- an electrode holder which is arranged so as to slide freely in relation to the aforementioned casing; and
- a screw rod which is screwed approximately to the center part of the electrode holder and is supported so as to rotate freely in relation to the aforementioned casing.

Furthermore, the brain electrode securing device according to the present invention is characterized in that a connector is secured to the casing and one end of a flexible baseboard is secured to the aforementioned electrode holder, one end of the wire of the aforementioned flexible baseboard is connected to the aforementioned connector and the other end of the wire of the aforementioned flexible baseboard is connected to the upper end of the aforementioned electrode wire.

In the brain electrode securing device according to the present invention, the electrode holder and the connector are assembled integrally in the casing. Therefore, installation operation can be completed only by mounting the casing on the skull so that the tip (the electrode) of the electrode wire fits into the hole in the skull and by securing the aforementioned casing to the skull by means of dental cement or the like.

To be precise, in the brain electrode securing device according to the invention, it is possible to ensure the screw rods are perpendicular by mounting the casing in the skull without taking into account the perpendicularity of the screw rods (perpendicularity of the electrode wire), but the electrode wire and the connector can be connected in advance so that the installation operation becomes simple.

In addition, the brain electrode securing device according to the present invention is characterized in that the casing of the device is of watertight construction and the aforementioned casing can be secured to the skull in a watertight fashion.

In the brain electrode securing device according to the invention, the casing is of watertight construction so that the underwater behavior of small animals can be assessed and yet, because no special cover is required, the device is compact and the mounting operation is easy.

The casing can be secured to the skull with a publicly known watertight construction and using publicly known materials which can be secured in a watertight fashion. For example, it is possible to use the dental cement employed in the prior art to secure the brain electrode securing device. However, in this case it is preferable to coat the outer surface of the dental cement with waterproof material.

In addition, the brain electrode securing device according to the present invention is characterized in that the casing is divided into upper and lower parts, the lower part of the casing is secured to the aforementioned skull and the upper part of he casing is connected to the aforementioned lower part of the casing.

In this brain electrode securing device according to the present invention, when it is desired to temporarily interrupt the measurement process, by detaching the upper part of the casing from the lower part of the casing it is possible to remove the main part of the device from the small animal so that the burden on it is relieved during periods when measurement is not being carried out.

The lower part of the casing can be secured to the upper part of the casing using publicly known connection means which can be connected in a watertight fashion.

Furthermore, the brain electrode securing device according to the present invention comprises a cover which is coupled to the upper portion of the aforementioned lower part of the casing and covers the opening in the upper portion of the aforementioned lower part of the casing.

In the brain electrode securing device, when the upper part of the casing is removed from the lower part of the casing the cover seals off the opening in the lower part of the casing and dirt and the like is prevented from entering the brain.

DESCRIPTION OF THE PREFERRED EMBODIMENTS

Figure 1:
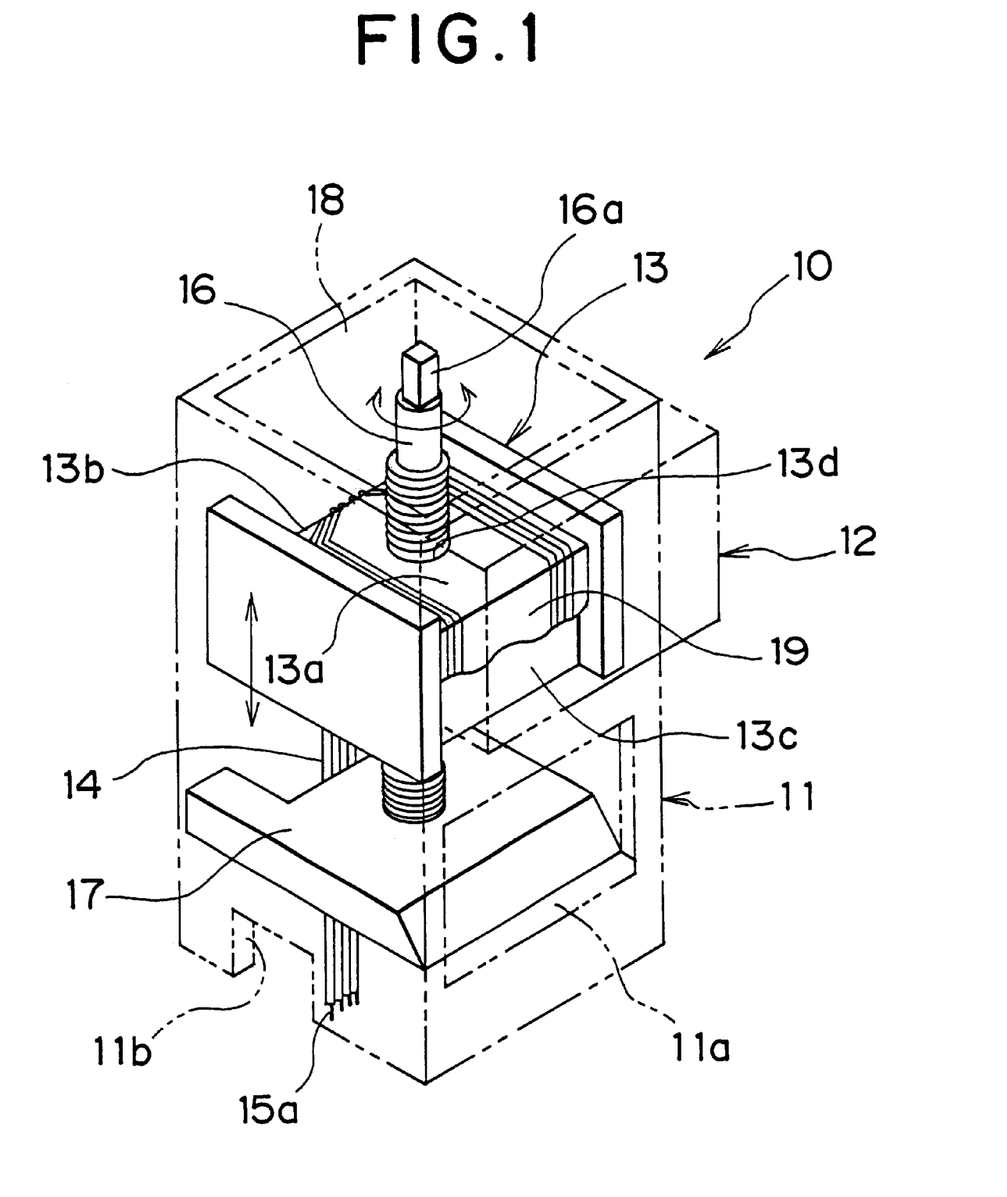
FIG. 1 is a general perspective view showing the main parts of the interior of an embodiment of the brain electrode securing device according to the invention.
Figure 2:
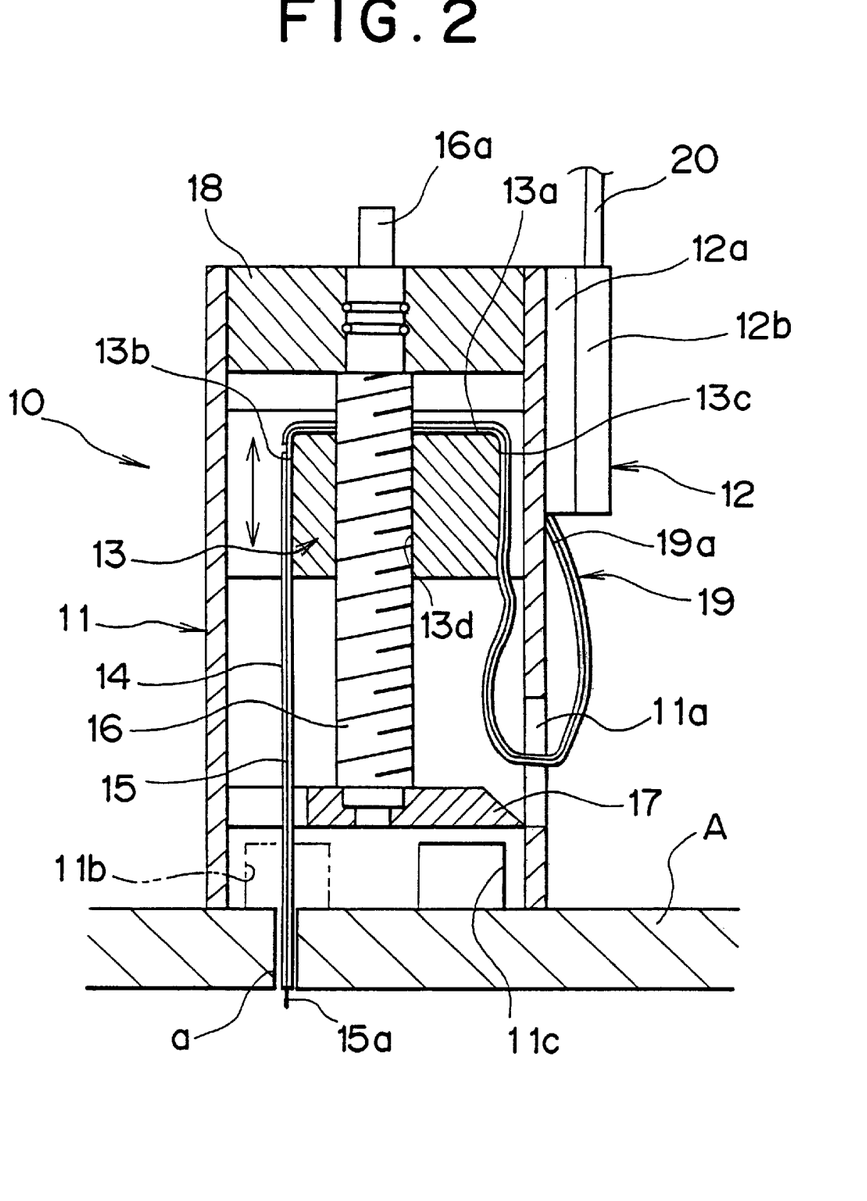
FIG. 2 is a section through the brain electrode securing device shown in FIG. 1, when it is installed on a skull.
Figure 3:
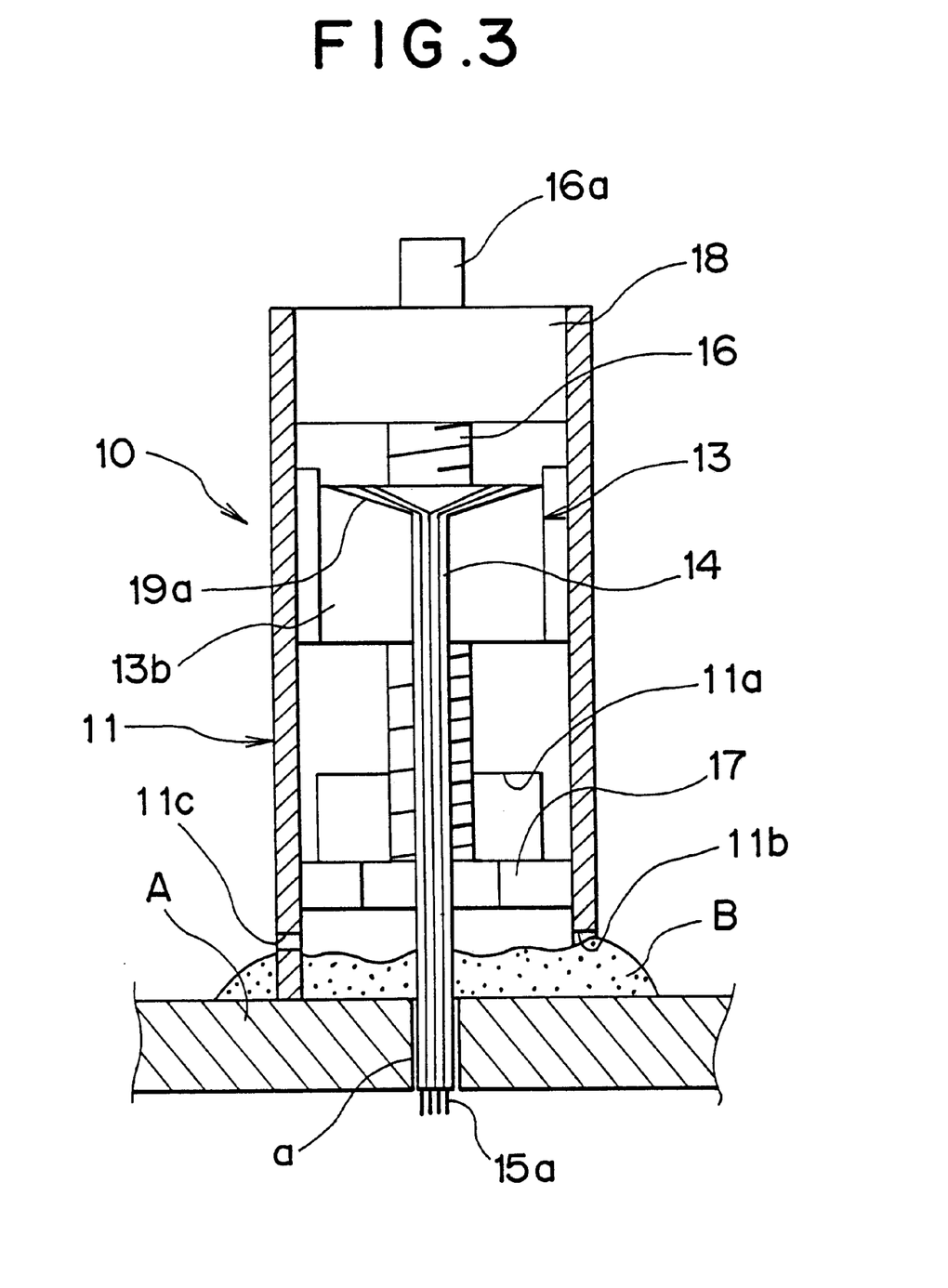
FIG. 3 is a different section through the brain electrode securing device shown in FIG. 1.

In the brain electrode securing device 10 as shown in FIGS. 1 to 3 the horizontal sectional face has a rectangular casing 11 which is made of transparent material. The socket 12a of the connector 12 is securely installed in the outer face of this casing 11 and the electrode holder 13 in arranged in the interior so as to be capable of sliding in the upward and downward directions. In the electrode holder 13, cutouts 13a, 13b and 13c are formed in the center of the upper part and in pairs of side faces lying opposite one another, and a female screw hole 13d extends from the center of the upper face to the center of the lower face, and furthermore the upper ends of guide tubes 14 extending in the downward direction are secured to the cutouts 13b. The electrode wire 15 is inserted into the guide tube 14.

The screw rod 16 is screwed into the female screw hole 13d of the aforementioned electrode holder 13, and the lower end and the upper part of the aforementioned screw rod 16 is supported so as to be freely rotatable in the plates 17,18 which are installed along the full width of the inside of the casing 11. Engagement means 16a which engage with a tool, such as a spanner, for turning the aforementioned screw rod 16 is formed in the end of this screw rod 16.

In addition, a flexible baseboard is arranged in the cutouts 13a, 13c in the electrode holder 13. The end of the afore-mentioned flexible baseboard 19 extends as far as the socket 12a of the connector 12 through the hole 11a formed in the side wall of the casing 11, and one end of the wire 19a of this flexible baseboard 19 is connected to the socket 12a of the connector 12. The other end of the wire 19a is connected to the upper end of the electrode wire 15. The socket 12a of this connector 12 is connected to the measuring device or the like (not shown in the figures) via the plug 12b and the wire 20.

A device 10 for securing a brain electrode constructed in this way is installed in the skull A of a small animal such as a mouse or a rat or the like in the manner presented below.

Firstly, when the tip of the guide tube 14 has been inserted, the hole a in the skull A is filled with dental cement B or the like through the cutouts 11b and 11c formed in the upper part of the casing 11, and, as shown in FIG. 3, the guide tube and the casing 11 are secured to the skull A. When this has been done, grease or some similar lubricant is applied to the outer face of the aforementioned guide tube 14, because it is necessary for the aforementioned guide tube 14 to be able to slide in relation to the dental cement B.

Next, a spanner or some similar tool is engaged to the coupling means 16a on the screw rods 16 and the aforementioned tool is used to rotate the screw rod 16. The electrode holder 13 is then guided to the inner face of the casing 11 and the electrode wire 15 is lowered together with the guide tube 14 and the tip (electrode) 15a of the electrode wire 15 is inserted into the prescribed location inside the brain. While this is being done the conditions inside the casing 11 can be observed through the transparent casing 11.

In the embodiment above, the screw rod 16 is turned using the spanner or some other tool which is coupled to its upper end but it is also possible to provide a handle in the upper end of the screw rod 16 and to turn the screw rod 16 using the aforementioned handle. It is also possible to connect a miniature motor to the upper end of the screw rod 16 and to turn the screw rod 16 by means of the aforementioned motor.

Furthermore, by making either the screw rod 16 or the casing 11 serve as the base line and providing a scale on the other, it is possible to check the degree of rotation of the screw rod 16 and in this way check, from outside the casing 11, the degree of movement of the electrode holder 13, or in other words the degree of insertion of the electrode 15a.

Furthermore, in this embodiment the connector 12 is installed in the casing 11, the aforementioned connector 12 is connected to the measuring device or the like via the wire 20, and the aforementioned measuring device is used to measure the changes in electrical potential at the electrode 15a and to stimulate the nerve cells in the brain by means of a stimulator. In this case, the connector 12 or the measuring device may be optionally provided with signal transmitting and receiving means so that signals can be transmitted wirelessly between the measuring device and the connector 12.

Furthermore, in the aforementioned embodiment the electrode 13 is installed so as to slide freely while abutting directly against the inside of the casing 11, but a guide rail may be installed inside the casing 11 so that the electrode holder 13 can be guided by means of the aforementioned guide rail.

Figure 4:
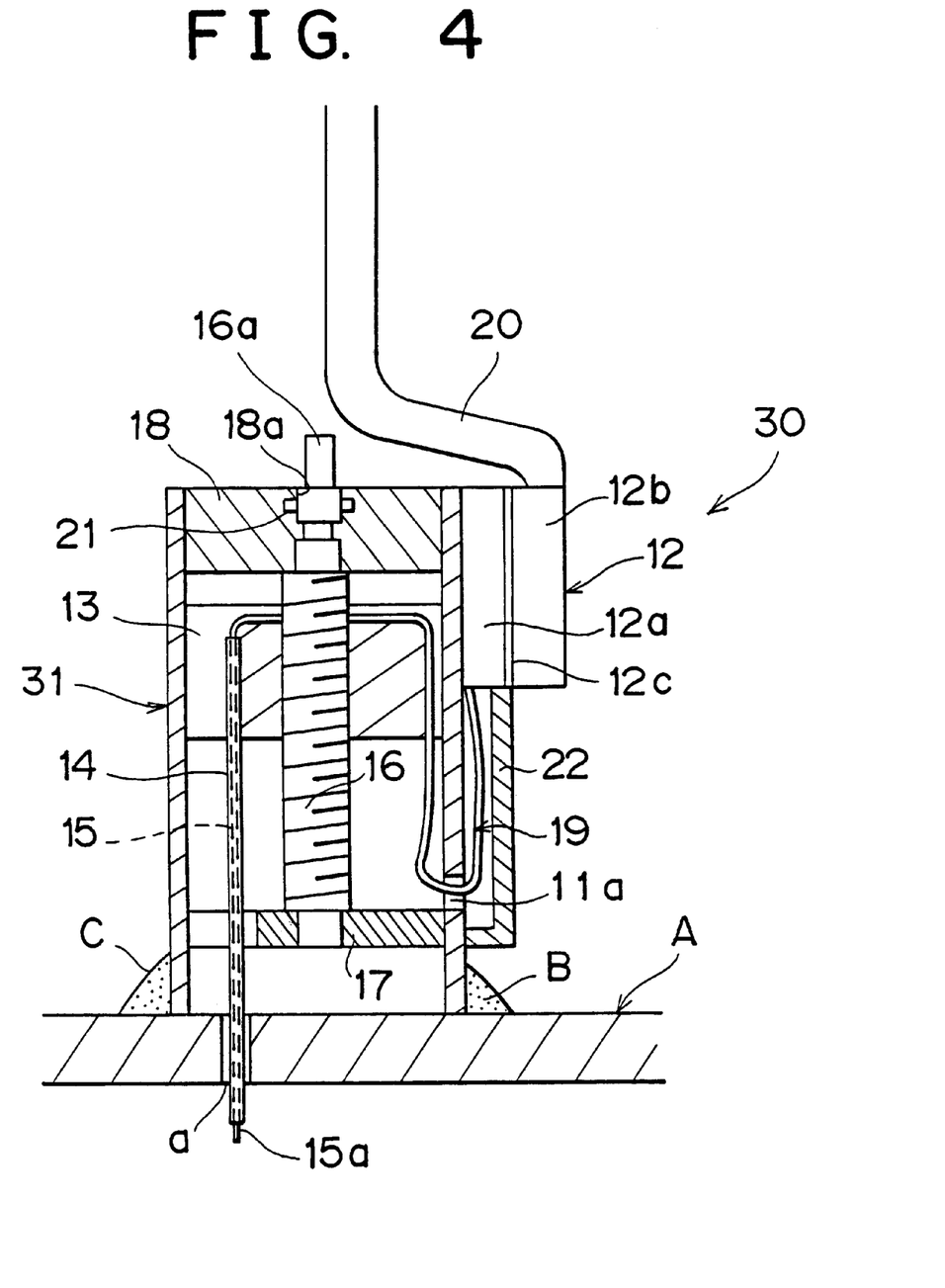
FIG. 4 is a section through another embodiment of the brain electrode securing device according to the present invention, when it is installed in the skull.

FIG. 4 shows another embodiment of the brain electrode securing device according to the invention.

This brain electrode securing device 30 is also of watertight construction and it is provided with the same main elements as the above embodiment of the brain electrode securing device 10. The main elements have therefore been provided with the same reference symbols as for the brain electrode securing device 10 and no further explanation has been given.

In this brain electrode securing device 30, at least the elements which forms the outer surface of the brain electrode securing device 30, such as the casing 11, the plates 18 which form the upper face of the aforementioned casing 31, and the components of the connector 12 and the like are made from a waterproof material such as a synthetic resin or the like and are coupled to one another in watertight fashion. However, the cutouts 11b, 11c formed in the casing 11 in the embodiment shown above are not formed in the casing 31 of this brain electrode securing device 30.

In this brain electrode securing device 30, packing is interposed between the socket 12a of the connector 12 and the plug 12b, and the socket 12a and the plug 12b are coupled to one another in watertight fashion.

Furthermore, in this brain electrode securing device 30, an O ring (sealing element) 21 is interposed between the upper part of the screw rod 16 and the hole 18a in the plate 18, and this ensures the watertight condition.

In addition, in this brain electrode securing device 30, a cover 22, which is made from a waterproof material such as a synthetic resin or the like, is arranged so as to cover the flexible baseboard 19 and the hole 11a which guides the aforementioned flexible baseboard 19 inside the casing 31. In fact, if the flexible baseboard 19 leads from the connector 12 to directly inside the casing 31, the hole 11a which guides the aforementioned flexible baseboard 19 inside the casing 31 becomes unnecessary and it is no longer necessary to provide the cover 22 either.

This casing 31 has the same main elements as the casing 11 in the embodiment above. Therefore the same symbols have been used in the figure so that no further explanation has been given.

Also, in this brain electrode securing device 30, the casing 31 is secured to the skull A in the same way as in the brain electrode securing device 10 of the embodiment above.

However, when dental cement B is employed as the securing means the outer surface of the aforementioned dental cement B is coated with a waterproof material C.

This brain electrode securing device 30 according to the invention is of watertight construction so that the underwater behavior of small animals can be assessed and yet, because no special cover is required, the device is compact and the mounting operation is easy.

Figure 5:
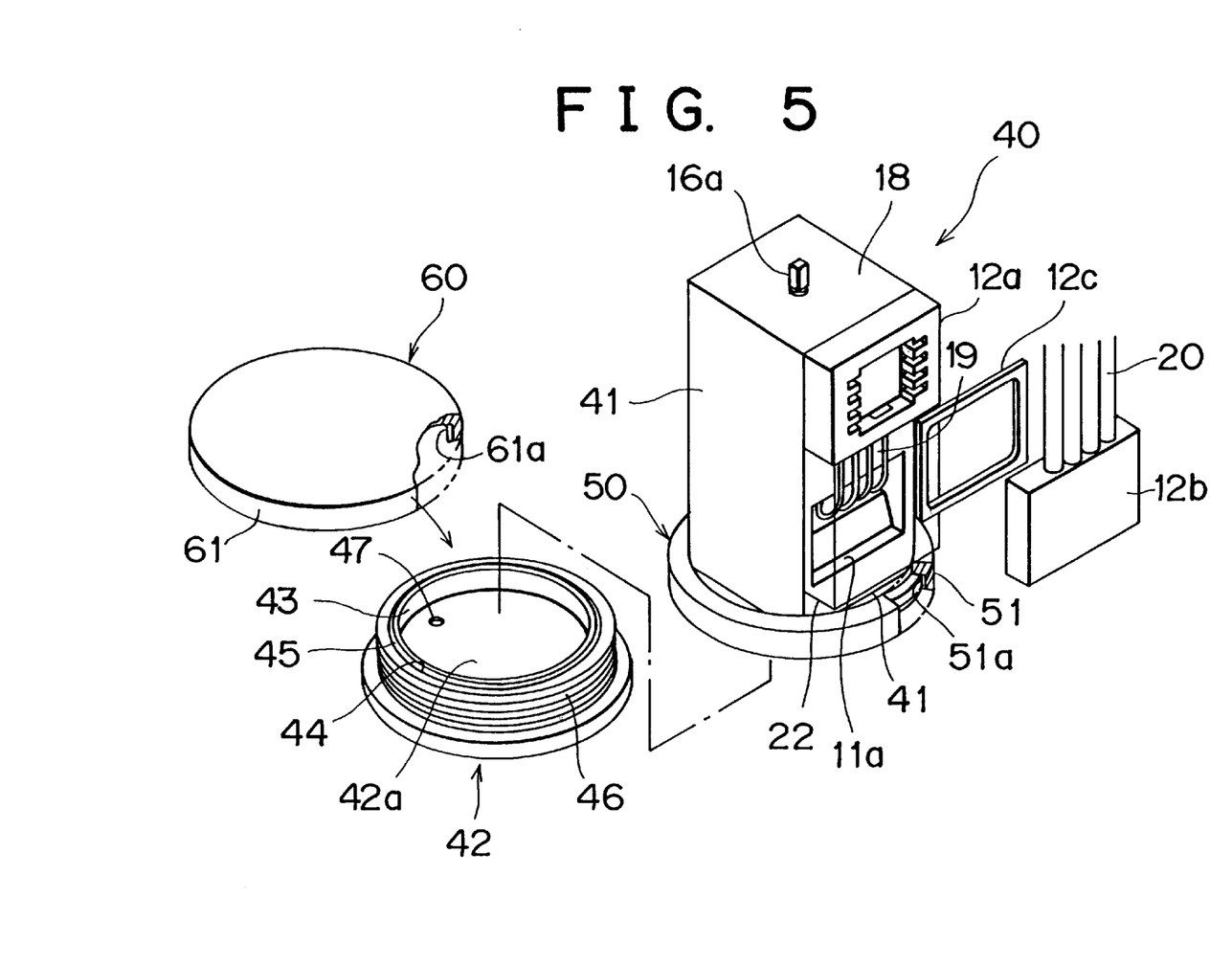
FIG. 5 is a general perspective view of a further embodiment of the brain electrode securing device according to the invention.
Figure 6:
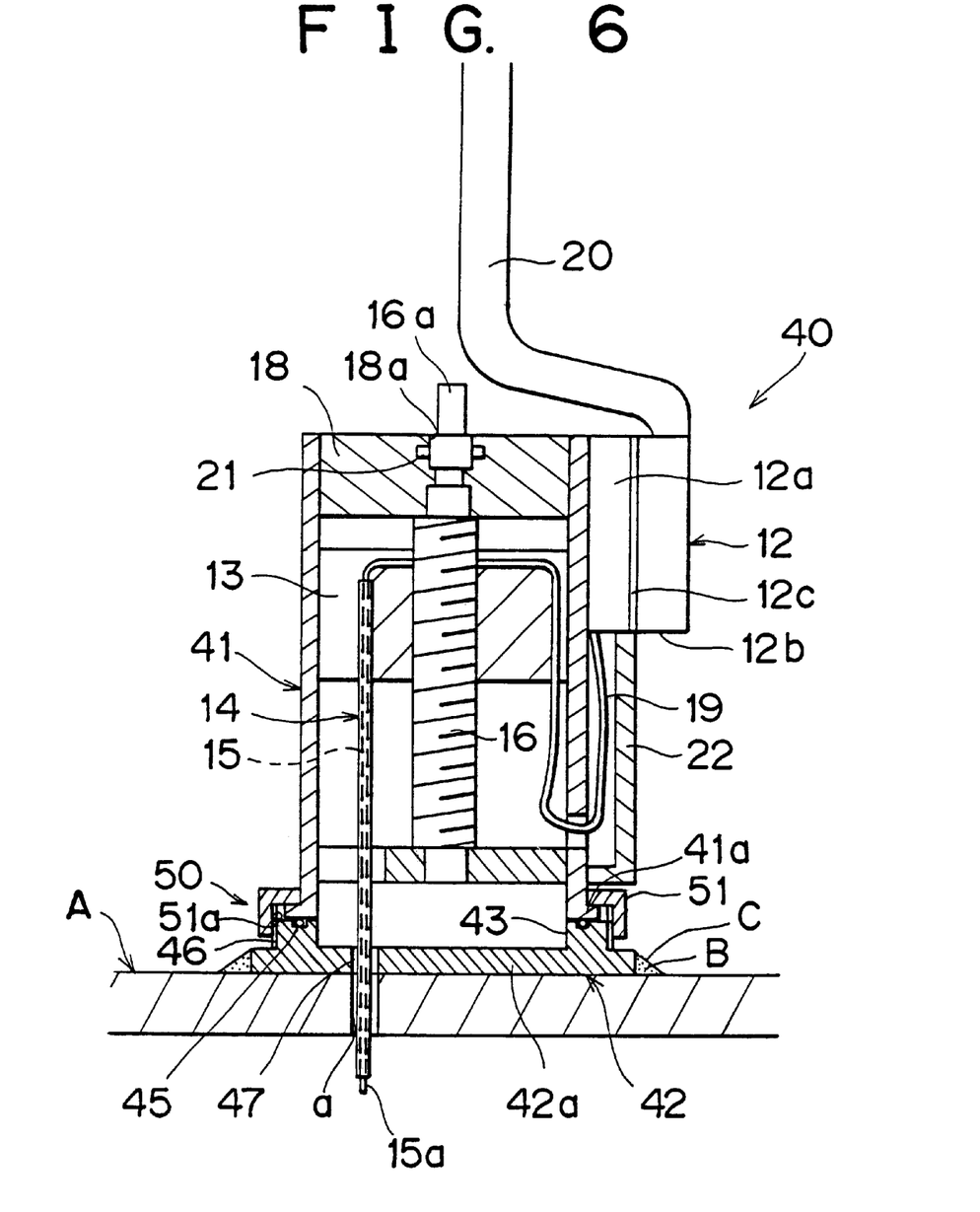
FIG. 6 is a section through the brain electrode securing device shown in FIG. 5, when it is installed in the skull.
Figure 7:
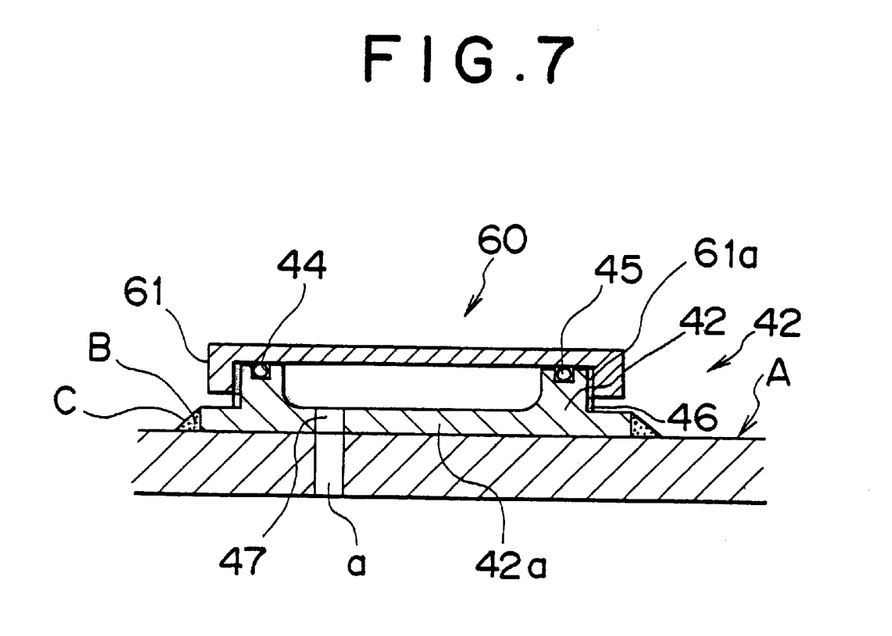
FIG. 7 shows a section through the brain electrode securing device when the device body is removed from its base and the base is covered by the cover.

In the brain electrode securing device 40 as shown in FIGS. 5 to 7, the casing which forms the outer surface of the device 40 is divided and is provided with a main casing part (upper part of the casing) 41 having essential elements such as an electrode holder 13, a screw rod 16, and a connector 12 which are the same as those arranged in the casing 11 of the device according to the embodiment above; the base (lower part of the casing) 42 which supports the main casing part 41 on the skull; coupling means 50 which connect the aforementioned base 42 and the main casing part 41, and a cover 60 which covers the opening in the upper part of the base 42 when the device is not in use.

In the main casing part 41, the horizontal section is formed into a rectangular tube shape using transparent materials in the same way as in the casing 11 of the aforementioned device 10. This main casing part 41 has a flange 41a protruding outward at the lower end. In fact, this main casing part 41 has the same main elements as in the casing 11 in the embodiment above and therefore the same reference symbols have been used as in the figures and no further explanation has been given.

The base 42 is constructed in the form of a tube with a bottom, using a waterproof material such as a gum or synthetic resin or the like, and it has circular ribs 43 on its upper face. Grooves 44 are formed in the upper face of the circular ribs 43 and circular packing 45 is accommodated in the aforementioned grooves 44. In addition, male screws 46 are formed in the outer circumference of the circular ribs 43, and the guide tube insertion hole 47 is formed in the bottom wall 42a.

In addition, the coupling means 50 is formed by a ring 51 having the side cross section in the shape of an L, and female screws 51a are formed in the internal circumferential face of the aforementioned ring 51. This coupling means 50 engages with play in the flange 41a of the main casing part 41.

In addition, the cover 60 is made of a waterproof material such as a gum or synthetic resin or the like and a circumferential wall which extends downward is formed on the outer surface and female screws 61a are formed in the internal circumferential face thereof.

Furthermore, in this brain electrode securing device 40, at least the components forming the outer surface of the device 40 such as the main casing part 41, the connector 12, the plate 18, the cover 22, the base 42 and the connection means 50 are made from a waterproof material and are coupled to one another in a watertight fashion.

In addition, in the same way as in the device 30 according to the embodiment above, O rings (sealing element) 21 are interposed between the upper part of the screw rods 16 and the holes 18a in the plates 18, and the aforementioned O rings ensures watertight condition between the screw rods 16 and the plates 18.

Furthermore, a brain electrode securing device 40 constructed in this way is installed in the skull A of a small animal such as a rat or the like in the following manner.

Firstly, as shown in FIG. 6, the base 42 is arranged on the skull A so that the hole 47 is aligned with the hole a which has been made in the skull A, and the aforementioned base 42 is secured to the skull A using securing means such as dental cement B or the like. When dental cement B is employed as the securing means, the outer surface of the dental cement B is coated with a waterproof material C.

Next, when the tip of the guide tube 14 has been inserted into the hole 47 in the base 42 and into the hole a in the skull A, the flange 41a on the main casing part 41 is arranged over the circular ribs 43 on the base 42 and the main casing part 41 is secured to the base 42 by screwing the female screw 51a of the ring 51 onto the male screw 46 of the circular rib 43. Then, the packing 45 is interposed between the flange 41a on the main casing part 41 and the upper face of the circular ribs 43 and this provides a watertight seal between the main casing part 41 and the base 42.

When measurement is interrupted over a comparatively long period, the casing element 41 can be detached from the base 42 and, as shown in FIG. 7, the cover 60 is secured to the base 42 by screwing the female screw of the cover 60 onto the male screw of the base 42. The cover 60 thus essentially seals off the hole a in the skull A.

When measurement is resumed, the cover 60 is detached from the base 42 and the aforementioned main casing part 41 is installed on the base 42 again.

In the casings 11, 31, 41 of the aforementioned a brain electrode securing devices 10, 30, 40 the horizontal section is in the form of a rectangular tube but, of course, the horizontal section may also be of a circular tube (cylindrical).

What is claimed is:

1. A brain electrode securing device in which an electrode-wire electrode held by an electrode holder is inserted into the brain through a hole formed in the skull in order to measure such things as changes in electrical potential by means of said electrode at a measuring location inside the brain, comprising:

a casing that is adapted to mount on the skull so as to surround said hole;

a connector that is secured to said casing;

said electrode holder being arranged within said casing so as to slide freely in relation to said casing;

a flexible baseboard having one end secured to said electrode holder, said flexible baseboard including a wire, one end of said wire of said flexible baseboard being connected to said connector and another end of said wire of said flexible baseboard being connected to an upper end of said electrode-wire electrode, and a screw rod that is screwed approximately to a center of said electrode holder and supported so as to rotate freely in relation to said casing.

2. The brain electrode securing device as claimed in claim 1 that is made of a watertight construction.

3. A brain electrode securing device in which an electrode-wire electrode held by an electrode holder is inserted into the brain through a hole formed in the skull in order to measure such things as changes in electrical potential by means of said electrode at a measuring location inside the brain, comprising:

a casing that is adapted to mount on the skull so as to surround said hole, said casing being divided into upper and lower parts, said lower part of said casing being adapted to be secured to the skull, and said upper part of said casing being secured to said lower part of said casing;

said electrode holder being arranged within said casing so as to slide freely in relation to said casing;

a screw rod that is screwed approximately to a center of said electrode holder and supported so as to rotate freely in relation to said casing, and a cover which is coupled to an upper portion of said lower part of said casing and covers an opening in said upper portion of said lower part of said casing.

4. The brain electrode securing device as claimed in claim 3 that is made of a watertight construction.

* * * * *